United States Patent [19]
Wood

[11] Patent Number: 5,283,179
[45] Date of Patent: Feb. 1, 1994

[54] LUCIFERASE ASSAY METHOD

[75] Inventor: Keith V. Wood, Madison, Wis.

[73] Assignee: Promega Corporation, Madison, Wis.

[21] Appl. No.: 580,371

[22] Filed: Sep. 10, 1990

[51] Int. Cl.⁵ .............................................. C12Q 1/66
[52] U.S. Cl. ............................................ 435/8; 435/6
[58] Field of Search ......................................... 435/8, 6

[56] References Cited

U.S. PATENT DOCUMENTS

| | | | |
|---|---|---|---|
| 4,234,681 | 11/1980 | DeLuca-McElroy | 435/8 |
| 4,246,340 | 1/1981 | Lundin et al. | 435/8 |
| 4,614,712 | 9/1986 | Baldwin et al. | 435/4 |
| 4,833,075 | 5/1989 | Vijayalakshmi et al. | 435/8 |

OTHER PUBLICATIONS

Airth et al., "The Function of Coenzyme A in Luminescence" Biochim. et Biophys. Acta., 27 519–532 (1958).
Rhodes and McElroy, "The Synthesis and Function of Luciferyl–Adenylate and Oxyluciferyl–Adenylate," J. Biol. Chem., 233 1528–1537 (1958).
McElroy and Seliger, "The Chemistry of Light Emission," Advances in Emzymol. 25, 119–165 (1963).

*Primary Examiner*—Ronald W. Griffin
*Assistant Examiner*—Pamela S. Webber
*Attorney, Agent, or Firm*—Foley and Lardner

[57] ABSTRACT

The invention provides improved methods for assaying samples for the presence of a beetle luciferase. The methods of the invention entail improved kinetics of light production from luciferase activity in beetle luciferase-luciferin reactions.

13 Claims, 8 Drawing Sheets

FIG. 1
Effect of 1 mM Coenzyme A
(1 mM ATP, 1 mM $LH_2$, no DTT)

FIG. 6
Titration of Luciferase
(220 μl reaction volume — 60 second integration)

FIG. 3b

LUCIFERASE ASSAY METHOD

TECHNICAL FIELD

This invention relates generally to bioluminescence. More particularly, the invention concerns methods for improved light production from beetle luciferase activity and compositions for carrying out the methods. The invention is particularly well-suited for assays and test kits which use luciferase as a reporter or marker for quantitating products or occurrences of certain biospecific reactions.

BACKGROUND OF THE INVENTION

The use of reporter molecules or labels to qualitatively or quantitatively monitor molecular events is well established in assays used for medical diagnosis, for the detection of toxins and other substances in industrial environments, and for basic and applied research in biology, biomedicine, and biochemistry. Such assays include immunoassays, nucleic acid probe hybridization assays, and assays wherein production of a reporter molecule is due to transcription from a particular promoter. Reporter molecules or labels in such assay systems have included radioactive isotopes, fluorescent agents, enzymes and chemiluminescent agents.

Among the assay systems, in which chemiluminescence has been employed to monitor or measure events of interest, are those in which the activity of a bioluminescent enzyme, a luciferase, is measured. Use of luciferase assays, however, has not been widespread because of the brevity and pattern of the light emission in the assays. With beetle luciferases, this emission involves very rapid attainment of a peak intensity, i.e., a flash of light, followed by a slower, but still problematically rapid, decay to an even more slowly decaying "steady-state" intensity of, initially, approximately only about 10% of the peak intensity. The brevity of the intense light emission usually requires specialized laboratory procedures, such as rapid injection of the enzyme into a substrate solution, to prepare the bioluminescent reaction mixture in carrying out the assay. The need to measure the light emitted during the "flash" continues as a cause of experimental problems. It remains difficult, even with present day luminometers, to precisely measure such light.

Light-emitting systems have been known and isolated from many luminescent organisms, including certain bacteria, protozoa, coelenterates, molluscs, fish, millipedes, flies, fungi, worms, crustaceans, and beetles, particularly the fireflies of the genera Photinus, Photuris, and Luciola and click beetles of genus Pyrophorus. In many of these organisms, enzymatically catalyzed oxidoreductions take place in which the free energy change is utilized to excite a molecule to a high energy state. Then, when the excited molecule spontaneously returns to the ground state, visible light is emitted. This emitted light is called "bioluminescence."

Beetle luciferases, particularly that from the firefly species, *Photinus pyralis*, have served as paradigms for understanding of bioluminescence since the earliest studies. The *P. pyralis* luciferase is an enzyme which appears to have no prosthetic groups or tightly bound metal ions and has 550 amino acids and a molecular weight of about 60,000 daltons; the enzyme has been available to the art in crystalline form for many years. Studies of the molecular components in the mechanism of firefly luciferases in producing bioluminescence have shown that the substrate of the enzymes is firefly luciferin, a polyheterocyclic organic acid, D-(−)-2-(6′-hydroxy-2′-benzothiazolyl)-Δ$^2$-thiazolin-4-carboxylic acid (hereinafter referred to as "luciferin", unless otherwise indicated).

The beetle luciferase-catalyzed reaction which yields bioluminescence (hereinafter referred to simply as "the beetle luciferase-luciferin reaction") has been described as a two-step process involving firefly luciferin, adenosine triphosphate (ATP), and molecular oxygen. In the initial reaction, the luciferin and ATP react to form luciferyl adenylate with the elimination of inorganic pyrophosphate as indicated in the following reaction:

where E is the luciferase, LH$_2$ is the luciferin, Mg$^{2+}$ is magnesium ion, and PP$_i$ is pyrophosphate. The luciferyl adenylate, LH$_2$-AMP, remains tightly bound to the catalytic site of luciferase. When this form of the enzyme is exposed to molecular oxygen, the enzyme-bound luciferyl adenylate is oxidized to yield oxyluciferin (L=O) in an electronically excited state. The excited oxidized luciferin emits light on returning to the ground state as indicated in the following reaction:

One quantum of light is emitted for each molecule of luciferin oxidized. The electronically excited state of the oxidized luciferin is a state that is characteristic of the luciferase-luciferin reaction of a beetle luciferase; the color (and, therefore, the energy) of the light emitted upon return of the oxidized luciferin to the ground state is determined by the enzyme, since different species of beetles having the same luciferin emit light of different colors.

When light emission is initiated by injection of ATP into a reaction mixture containing luciferase, Mg$^{2+}$, and luciferin, where all components are near or at saturating concentrations, one observes a rapid increase in intensity followed by a rapid decrease in the first few seconds, followed by a further decay that may last hours. This decrease in the rate of reaction has been thought to be due to product inhibition.

Luciferase has been used as a means of assaying minute concentrations of ATP; as little as 10$^{-16}$ molar ATP can be detected with high quality preparations of the enzyme. The luciferase-luciferin reaction is highly specific for ATP. For example, deoxy-ATP produces less than 2% of the light generated by ATP, and other nucleoside triphosphates produce less than 0.1%.

Coupling the concentration of ATP with the activity of other enzymes has allowed luciferase to become a biochemical reporter molecule for these other enzymes as well as other compounds.

The availability of beetle luciferases for use as reporters in other assays is not a problem. Such uses have been limited, however, by the problematic kinetics of light emission in the luciferase-luciferin reaction. But for such problematic kinetics, readily available beetle luciferases could have been employed in applications, such as immunoassays, such as enzyme-linked immunosorbent assays, in which an enzyme serves as reporter, and nucleic acid probe hybridization assays, in which an enzyme serves as a reporter.

Beyond the availability of crystalline luciferases isolated directly from the light organs of beetles, CDNAS encoding luciferases of several beetle species (including, among others, the luciferase of *P. pyralis*(firefly), the four luciferase isozymes of *P. plagiophthalamus*(click beetle), the luciferase of *L. cruciata*(firefly) and the luciferase of *L. lateralis*)(de Wet et al., Molec. Cell. Biol. 7, 725-737 (1987); Masuda et al., Gene 77, 265-270 (1989); Wood et al., Science 244, 700-702 (1989); European Patent Application Publication No. 0 353 464) are available. Further, the CDNAS encoding luciferases of any other beetle species, which make luciferases, are readily obtainable by the skilled using known techniques (de Wet et al. Meth.Enzymol. 133, 3-14 (1986); Wood et al., Science 244, 700-702 (1989). With the cDNA encoding a beetle luciferase in hand, it is entirely straightforward for the skilled to prepare large amounts of the luciferase in highly pure form by isolation from bacteria (e.g., *E. coli*), yeast, mammalian cells in culture, or the like, which have been transformed to express the CDNA. Various cell-free systems, that have recently become available to make proteins from nucleic acids encoding them, can also be used to make beetle luciferases.

Further, the availability of CDNAS encoding beetle luciferases and the ability to rapidly screen for CDNAS that encode enzymes which catalyze the luciferase-luciferin reaction (see de Wet et al., Meth. Enz., supra, and Wood et al., supra) also allow the skilled to prepare, and obtain in large amounts in pure form, mutant luciferases that retain activity in catalyzing production of bioluminescence through the luciferase-luciferin reaction. Such a mutant luciferase will have an amino acid sequence that differs from the sequence of a naturally occurring beetle luciferase at one or more positions. In the present disclosure, the term "beetle luciferase" comprehends not only the luciferases that occur naturally in beetles but also the mutants, which retain activity in providing bioluminescence by catalyzing the luciferase-luciferin reaction, of such naturally occurring luciferases.

The ready availability of CDNAS encoding beetle luciferases makes possible the use of the luciferases as reporters in assays employed to signal, monitor or measure genetic events associated with transcription and translation, by coupling expression of such a CDNA, and consequently production of the enzyme, to such genetic events.

Thus, while the potential uses for beetle luciferases as reporter molecules have become increasingly important and quite varied, the brevity and pattern of the light emission caused by the enzymes has limited their utility in practice. It would be desirable to enhance the utility of beetle luciferases as reporters by effecting with them more efficient light production, i.e., light emission at a more nearly continuous, yet high, rate.

One approach, which achieved some popularity, to solving the problem of the kinetics of the luciferase-luciferin reaction and the associated difficulty of precisely measuring light emitted during the flash, was to use various inhibitors of the enzyme, which were reported to prevent the flash from occurring or to prolong light production. One such agent is arsenate. Arsenate lowers flash height and tends to prolong the light emission for a given amount of ATP but reduces sensitivity for detecting ATP. While luciferase preparations containing arsenate remained commercially available until recently, use of such preparations is no longer favored. In part this is because the need for such use can be avoided in some applications with the use of sophisticated light-measuring instrumentation.

However, even with such sophisticated instrumentation, specialized laboratory procedures, such as an injection format for rapidly mixing the enzyme and substrate, are still required. Improving the kinetics of light production for the enzymatic reaction, to avoid the need for such specialized and cumbersome procedures, would greatly expand the utility of luciferases as reporters.

A number of compounds, besides arsenate salts, has also been reported to affect the pattern of light production from the beetle luciferase-luciferin reaction. Phosphate salts were employed for the same purpose as the arsenate salts but were not favored because the required presence of magnesium ion in the assay systems led to the undesirable precipitation of magnesium phosphate when phosphate salts were used.

The cofactor, coenzyme A (CoA), has been reported to affect the pattern of light emission in the luciferin-luciferase reaction. Airth et al., Biochimica et Biophysica Acta, vol. 27 (1958) pp. 519-532, report that, when CoA is added to a firefly luciferin-firefly luciferase reaction mixture, there is no effect on the initial peak of light intensity but luminescence will continue at a higher level for a time period that is proportional to the total CoA added. Airth et al. have shown that the total light emitted is greater in the presence of CoA than in its absence.

Airth et al. also report that cysteine and glutathione do not stimulate light emission and, without providing details, that hydroxylamine stimulates and thioethanolamine slightly stimulates emission in a manner similar to CoA.

The teaching of Airth et al. concerning the effect of CoA on light emission from the beetle luciferase-catalyzed reaction of luciferin, ATP and oxygen, is suspect. Subsequent to the Airth et al. report, the effect of CoA on luciferase was explained on the basis of prevention by CoA of inhibition of the enzyme by dehydroluciferin, a compound thought to be a significant contaminant of the luciferin used by Airth et al. and subsequent workers, who purified the luciferin from fireflies. Luciferin employed in more recent times, and today, is prepared synthetically and, as such, is substantially free of dehydroluciferin. Synthetic preparations of luciferin typically are contaminated with less than 1%, and preferably less than 0.3%, dehydroluciferin by weight relative to luciferin. Thus, CoA would be expected to have no effect on luciferase activity with synthetically prepared luciferin. The teaching of Airth et al. and subsequent workers on stimulation of light emission with beetle luciferases by CoA (and other compounds mentioned in the Airth et al. reference) has been completely ignored for more than 30 years in efforts to broaden the practical applicability of assays based on luciferase-catalyzed light emission. For example, CoA has never been suggested as a substitute for arsenate, notwithstanding the recognized undesirability of arsenate.

It has also been reported that other sulfhydryl compounds contribute to the stability of luciferases during preparation and storage of the enzymes. U.S. Pat. No. 4,833,075 discloses that dithiothreitol (DTT) will maintain luciferase activity at a level of 50% in an aged

*Photinus pyralis* luciferase solution which, without the DTT, would have only 10% residual enzymatic activity compared to a freshly prepared luciferase solution. U.S. Pat. No. 4,614,712 describes that, when bacterial luciferase has been inactivated by disulfide formation, enzyme activity may be restored by addition of DTT, β-mercaptoethanol (β-ME), or other reducing agents. Although beetle luciferases and bacterial luciferases differ in structure and action, both appear to have a reactive sulfhydryl group which may be protected from general oxidation by certain reducing agents.

However, it has been thought in the art that dithiothreitol (DTT) and similar thiol reagents, at concentrations above about 5 mM, would inhibit light emission catalyzed by luciferases.

Despite recognition and study of various aspects of the chemistry of luciferases, the prior art has provided little in the way of practical techniques for more efficient light production from the luciferase-luciferin reaction to increase the utility of the resulting luminescence as a detection mode.

SUMMARY OF THE INVENTION

The present invention provides improvements in the kinetics of light production in beetle-luciferase-luciferin reactions and entails various discoveries relating to the chemistry of such light production. The improved kinetics of light production are associated with chemistry that slows or reduces product inhibition of luciferase in the luciferase-luciferin reaction and slows inactivation of the luciferase that occurs during catalysis of the light-producing reaction.

The improved kinetics are also attributable in part to two previously unrecognized compositions: the thioester of CoA and luciferin and the complex of CoA, luciferase and oxidized luciferin in its excited state. The invention encompasses these compositions.

It has been discovered that including CoA, or a thiol reagent such as DTT, or both in a beetle luciferase-luciferin reaction mixture provides surprising improvements in the kinetics of light production from the reaction and in the total yield of light from the reaction. Further, it has been discovered that including CoA in a beetle luciferase-luciferin reaction mixture and then subjecting the mixture to some other chemical or physicochemical condition whereby the peak intensity of bioluminescence from the reaction is reduced by a small amount has the advantageous effect of increasing the total yield of bioluminescence from the reaction. Thus, the present invention provides improved methods, and compositions and test kits for carrying out the methods, for using the beetle luciferase-luciferin reaction, and the bioluminescence produced thereby, to test or assay samples for the presence of a beetle luciferase, for genetic events in such samples (e.g., of cells) that lead to production of a beetle luciferase, for the presence of ATP, or for chemical or biochemical events that lead to production of ATP. In these methods, and with these compositions and test kits, of the invention, the kinetics of light production from the beetle luciferase-luciferin reaction is improved by virtue of a reduced ratio of peak intensity to the total yield of such light and increased total yield of the light or by virtue of a reduction in the rate at which the intensity decreases after the peak intensity is achieved.

An advantage of the present invention is that it provides beetle luciferase-luciferin reactions with kinetics of light production, from which the "flash," that has plagued the reaction in the prior art, is significantly reduced but with total yield of light that is significantly increased, typically by more than 10-fold, over such reactions in the prior art. Such improvements in the kinetics of light production and the total light produced in the beetle luciferase-luciferin reaction render assaying for luciferase, or for ATP using luciferase, significantly simpler and more sensitive than with prior art methods. For example, with the methods and compositions or test kits of the present invention, the assays do not require special procedures, such as rapid sample injection, or special equipment, such as sophisticated luminometers, to measure the light emitted in the rapid flash of conventional luciferase-luciferin reactions.

Indeed, using the methods and compositions or kits of the present invention, it is now possible that devices, such as scintillation counters, that are already available in laboratories for other types of measurements, can now be employed in assays requiring measurement of light produced in a beetle luciferase-luciferin reaction; this could significantly expand application of such assays in science and technology by facilitating use of the assays in laboratories that do not have luminometers but do have scintillation counters or other devices for measuring light production. Heretofore, the kinetics of light production from the luciferase-luciferin reaction precluded the use of scintillation counters in assays requiring measurements of such light.

With the present invention, the full potential of beetle luciferases as markers or reporter molecules can be realized in practice.

Other advantages and a fuller appreciation of specific adaptations, compositional variations, and physical attributes will be gained upon an examination of the following detailed description of the invention, taken in conjunction with the accompanying figures of the drawings.

BRIEF DESCRIPTION OF THE DRAWINGS

The present invention will hereinafter be described in conjunction with the appended drawings, wherein like designations refer to like elements throughout and in which.

DETAILED DESCRIPTION

In the following description, process steps are carried out and concentrations are measured at room temperature (about 20° C. to about 25° C.) and atmospheric pressure unless otherwise specified.

As used herein, the term "luciferase," unless specified otherwise, refers to a naturally occurring or mutant beetle luciferase. The luciferase, if naturally occurring, may be obtained easily by the skilled from the beetle itself, and particularly the light organ thereof. If the luciferase is one that occurs naturally or is a mutant, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding same. The preferred luciferase is that of the firefly *Photinus pyralis*.

The term "luciferin" is defined above.

In one of its aspects, the invention is a method for detecting the presence of a beetle luciferase in a sample suspected of containing the luciferase, comprising (a) making with an aliquot of said sample a solution comprising, at concentrations effective for activity of the luciferase in the luciferase-luciferin reaction, luciferin, adenosine triphosphate, a thiol reagent, and $Mg^{2+}$; and (b) measuring luminescence from the solution resulting from step (a). This first-aspect of the invention entails simply taking a portion (i.e., an aliquot) of a sample to be analyzed (e.g., an extract of a mammalian cell culture in the cells of which the luciferase might have been expressed or not expressed if a promoter controlling such expression was active, or inactive, respectively), combining the aliquot with a solution, in which the luciferase, if present, will be active in the luciferase-luciferin reaction, and which comprises a thiol reagent, and measuring the solution (or a part of it) to ascertain whether bioluminescence is being produced in it. The combining of the aliquot of sample with such a solution will preferably, and usually, entail simple dissolution of all components of the aliquot in the solution. In any case, the combining must be such that luciferase, if present in the aliquot, will become dissolved in the solution, where the reaction underlying the assay method takes place. As the skilled will understand, this method of the invention, being an assay method, will usually be carried out with suitable controls or standards (e.g., a sample being analyzed will be analyzed in parallel with solutions with no luciferase and with known concentrations of luciferase) and, with appropriate standards, the method can be adapted to quantitating the concentration of the beetle luciferase in a test sample (i.e., a sample being analyzed).

As noted below, because of the improved kinetics of light production from the luciferase-luciferin reaction provided by the present invention, the assay method of the invention for luciferase can detect the enzyme over a range from about $10^{-18}$ M to about $10^{-6}$ M, with the lower limit being limited only by the noise in even the best available light-detecting apparatus.

Beetle luciferases differ somewhat in the ranges of conditions, of pH, ionic strength, temperature, ATP concentration, magnesium ion concentration, luciferin concentration, and the like, over which they are active in the luciferase-luciferin reaction. It is, however, a simple matter for a skilled artisan to ascertain such ranges, and even the optimum ranges, for any particular beetle luciferase.

The skilled are also aware that compositions other than those specifically recited above will be or may be present in any assay reaction mixture, in order to, for example, maintain or enhance the activity of the enzyme or as a consequence of the procedures used to obtain the aliquot of sample being subjected to the assay procedures. Thus, typically buffering agents, such as tricine, HEPPS, HEPES, MOPS, Tris, glycylglycine, a phosphate salt, or the like, will be present to maintain pH and ionic strength; a proteinaceous material, such as a mammalian serum albumin (preferably bovine serum albumin) or lactalbumin or an ovalbumin, that enhances the activity of luciferases in the luciferase-luciferin reaction, may be present; EDTA or CDTA (cyclohexylenediaminetetraacetate) or the like, may be present, to suppress the activity of metal-containing proteases or phosphatases that might be present in systems (e.g., cells) from which luciferase to be assayed is extracted and that could adversely affect the luciferase or the ATP. Glycerol or ethylene glycol, which stabilize luciferases, might be present. Similarly, detergents or surfactants, particularly nonionic detergents, such as those of octoxynol (e.g., sold under the trademark "Triton X" of Rohm & Haas, such as Triton X-100) might be included, typically as remnants, carried into a solution used in an assay according to the invention, of a solution used to lyse cells from which luciferase is extracted for the assay. Counterions to the magnesium will, of course, be present; as the skilled will understand, the chemical identities and concentrations of these counterions can vary widely, depending on the magnesium salt used to provide the magnesium ion, the buffer employed, the pH of the solution, the substance (acid or base) used to adjust the pH, and the anions present in the solution from sources other than the magnesium salt, buffer, and acid or base used to adjust pH. In one procedure, the magnesium ion can be supplied as the carbonate salt, to provide the desired magnesium ion concentration, in a solution with the buffer to be used (e.g., tricine) and then the pH of the buffered solution can be adjusted by addition of a strong acid, such as sulfuric, which will result in loss of most of the carbonate (and bicarbonate) as carbon dioxide and replacement of these anions with sulfate, bisulfate, tricine anion, and possibly also other types of anions (depending on other substances (e.g., phosphate salts) that provide anions and might be present in the solution). Oxygen-saturation from the air of the solution in which the assay method is carried out is sufficient to provide the molecular oxygen required in the luciferase-luciferin reaction. In any case, it is well within the skill of the ordinarily skilled to readily ascertain the concentrations of the various components in an assay reaction mixture, including the components specifically recited above in the description of the method, that are effective for activity of the luciferase in the luciferase-luciferin reaction. The component that is essential to the improved kinetics of light production is the thiol reagent.

The thiol reagents used in the methods and compositions of the invention are CoA or thiol reagents other than CoA. The thiol reagents other than CoA are reagents which have a free sulfhydryl group that is capable of being effective as a reducing agent in an air-saturated aqueous solution under conditions, of temperature, pH, ionic strength, chemical composition, and the like, at which the luciferase-luciferin reaction occurs. Preferred among these reagents is dithiothreitol. Among others which can be employed are $\beta$-mercaptoethanol ($\beta$-ME), 2-mercaptopropanol (either enantiomer or both enantiomers in any combination), 3-mercaptopropanol, 2,3-dithiopropanol, and glutathione.

The types of samples which can be assayed for a luciferase in accordance with the method of the invention include, among others, samples which include a luciferase that had been used as a reporter in an immunoassay or samples which include a luciferase that had been used as a reporter in a nucleic acid probe hybridization assay. As understood in the immunoassay and nucleic acid probe arts, the luciferase assayed in accordance with the present invention will have been chemically linked, by any of numerous methods known in those arts, to an antibody or nucleic acid probe used in detecting an analyte in an immunoassay or nucleic acid probe hybridization assay, respectively. Then, also following well known methods, the luciferase-labeled antibody or nucleic acid probe will have been combined with a sample to be analyzed, to become bound to an analyte (e.g., antigen or an anti-antigen antibody, in the case of an immunoassay, or a target nucleic acid, in the case of a nucleic acid probe hybridization assay) that is sought to be detected and might be present in the sample and then luciferase-labeled antibody or nucleic acid probe that did not become bound to analyte will have been separated from that, if any, which did become bound. The sample to be assayed in accordance with the present invention will be of luciferase that was label on luciferase-labeled antibody or nucleic acid probe that bound to the analyte of such antibody or probe. The luciferase can remain chemically linked to the labeled antibody or probe during the assay for luciferase in accordance with the present invention or, again by known methods, can have been separated from the labeled antibody or nucleic acid probe prior to the assay for luciferase in accordance with the present invention. Immunoassays and nucleic acid probe hybridization assays, in which a beetle luciferase can be used as a reporter or label, have many practical and research uses in biology, biotechnology, and medicine, including detection of pathogens, detection of genetic defects, diagnosis of diseases, and the like.

Another type of sample which can be assayed for the presence of a luciferase in accordance with the method of the invention is an extract of cells in which expression of the luciferase occurs in response to activation of transcription from a promoter, or other transcription-regulating element, linked to a DNA segment which encodes the luciferase, or as a result of translation of RNA encoding the luciferase. In such cells, luciferases are used, similarly to the way other enzymes, such as chloramphenicol acetyltransferase or beta-galactosidase, have been used to monitor genetic events such as transcription or regulation of transcription. Such uses of beetle luciferases are of value in molecular biology and biomedicine and can be employed, for example, in screening of compounds for therapeutic activity by virtue of transcription-activating or transcription-repressing activity at particular promoters or other transcription-regulating elements.

In another of its aspects, the invention entails a method of detecting ATP. This method follows from the aspect of the invention involving the method for assaying for luciferase by virtue of the fact that ATP is required for the production of bioluminescence and differs from the method of assaying for luciferase only in that a beetle luciferase but not ATP is a required component in the assay reaction mixture. The method of the invention for detecting the presence of adenosine triphosphate in a sample suspected of containing said compound, comprises (a) making with an aliquot of said sample a solution comprising a beetle luciferase, luciferin, a thiol reagent, and $Mg^{2+}$, all at concentrations effective for activity of the luciferase in the luciferase-luciferin reaction; and (b) measuring luminescence from the solution resulting from step (a). As the skilled will readily appreciate, by carrying out this method of the invention with appropriate standards of varying, known concentrations of ATP together with samples of unknown concentration of ATP, the method can be adapted to determining the concentrations of ATP in the samples of unknown concentration. The ATP in samples being analyzed can arise from any of a variety of biochemical events or reactions, e.g., blood platelet aggregation. Thus, this method of the invention for assaying for ATP can be used to monitor the events or reactions that produced the ATP.

Preferably, in the methods (and compositions) of the invention, the luciferin that is used is synthetically prepared; both CoA and a thiol reagent other than CoA are employed or present; and in compositions of the invention which are solutions, the CoA is present at a concentration between about 0.1 mM and about 1.0 mM, and the thiol reagent other than CoA is present at a concentration between about 20 mM and 100 mM.

In still another of its aspects, the invention entails a composition which comprises a beetle luciferase, which is capable of catalyzing the luciferase-luciferin reaction, CoA and a thiol reagent other than CoA. Such compositions are preferably aqueous solutions but may, for example, be a lyophilized mixture of components. By "capable of catalyzing the luciferase-luciferin reaction" is meant that either the enzyme in the composition as is can catalyze the reaction or that the composition can be reconstituted, dissolved, or otherwise treated chemically or physically so that the enzyme becomes active in catalyzing the reaction. If the enzyme were irreversibly inactivated or inhibited, it would not be "capable of catalyzing the luciferase-luciferin reaction." The compositions according to the invention provide markedly improved kinetics of light production in the luciferase-luciferin reaction and are used in assays according to the invention, test kits according to the invention, standards in assays and test kits according to the invention, and in preparing assay mixtures and test kits of the invention as well as standards for use in the mixtures and kits. As described in some detail elsewhere in the present specification, the compositions can include numerous other components besides the essential three, a beetle luciferase capable of activity as described, CoA and a thiol reagent other than CoA.

The invention also entails test kits for carrying out the assay methods of the invention. Such kits comprise, in one or more containers, usually conveniently packaged to facilitate use in assays, quantities of various compositions essential for carrying out the assays in accordance with the invention. Thus, in kits for assaying for luciferase, there will be a composition, referred to as a "luciferase-luciferin reaction composition," which comprises, in addition to magnesium ion, ATP and luciferin, well known to be essential for the reaction, also a thiol reagent. Such composition will preferably comprise both CoA and a thiol reagent, such as DTT, other than CoA, and may comprise other components, such as, for example, a proteinaceous luciferase-activity enhancer (e.g., bovine serum albumin), EDTA or CDTA, a phosphate salt or 2-aminoethanol (see below), or a buffer to provide a solution at a pH and ionic strength at which the beetle luciferase-luciferin reaction will proceed at a suitable rate. The luciferin in the kit is preferably prepared synthetically. As indicated, the various components can be combined, e.g. in solution or a lyophilized mixture, in a single container or in various combinations (including individually) in a plurality of containers. In a preferred kit for assaying for luciferase in cells, in which the luciferase is expressed, there will also be included a solution (or the components for preparing a solution) useful for lysing the cells while preserving (against the action of various enzymes released during lysis) luciferase that might be in the cells in an active form, or a form which can be made active.

The test kits for assaying for ATP are similar to those for assaying for luciferase, except that such kits include a beetle luciferase in place of ATP.

The test kits of the invention can also include, as well known to the skilled, various controls and standards, such as solutions of known luciferase or ATP concentrations, including no luciferase or ATP (negative control), to ensure the reliability and accuracy of the assays carried out using the kits, and to permit quantitative analyses of samples for the analytes (e.g., luciferase, ATP) of the kits.

In another aspect, the invention encompasses an improvement in methods of assaying for the presence of substances (e.g., ATP, substances which result in the production of ATP, luciferase) in a sample, which methods comprise measuring light produced in a beetle luciferase-luciferin reaction. The improvement comprises carrying out the luciferase-luciferin reaction in the presence of CoA under conditions which reduce the peak intensity of light produced in the reaction by a small amount (e.g., between about 3% and about 30% relative to the peak intensity in the absence of such conditions). This aspect of the invention rests on the discovery that altering the conditions, under which a luciferase-luciferin reaction proceeds in the presence of CoA, so that the peak intensity of light production from the reaction is reduced by a small amount, results in an increase in the total light emitted in the reaction (i.e., as measured by integration of the intensity vs. time curve). This is advantageous in that it entails flattening of the intensity vs. time curve for light produced in the reaction and, thereby, renders measurement of the total light output simpler and more accurate. Of course, in a set of reaction systems which are the same except that peak intensities are reduced to different extents, because the condition employed to reduce peak intensities, although the same condition is applied in each system, is altered to different extents, a greater reduction in the peak intensity will require the luciferase-luciferin reaction to proceed for a longer time before an increase in total light output (measured by integrating the intensity vs. time curve from the initiation of the reaction) is realized, in comparison with the total output from the system in which the condition is not applied, so that peak intensity is not reduced; see, e.g., FIG. 8. A variety of conditions can be altered to effect the small decrease in peak intensity. Thus, for example, the pH, ionic strength or temperature of the reaction can be changed, in ways that are easily ascertained by the skilled and vary somewhat depending on the particular beetle luciferase involved, so that the peak intensity is reduced; or various substances which are inhibitors of luciferase can be included at appropriate concentrations in the solution in which the luciferase-luciferin reaction is to proceed. Among such substances are 2-aminoethanol, at a concentration between about 10 mM and about 100 mM, and phosphate at a concentration between about 5 mM and about 60 mM (see FIGS. 7 and 8). The improvement applies as well to the novel methods of the present invention, e.g., 36 mM 2-aminoethanol or 25 mM phosphate may be included in a luciferase-luciferin reaction mixture wherein not only CoA but also a thiol reagent other than CoA is present.

The mechanisms thought to underlie the invention are not completely understood, and reference herein to such mechanisms should not be construed to limit the scope of the invention.

It has been discovered that CoA interacts with the enzyme and electronically excited oxyluciferin during catalysis of the luciferase-luciferin reaction and, as one consequence of this interaction, reduces product inhibition of the enzyme in the course of a luciferase-luciferin reaction. (Oxyluciferin, otherwise referred to herein as "oxidized luciferin," differs from luciferin in having an oxygen in place of the hydrogen and carboxylate at the 4-position of the thiazoline ring in luciferin.) Thus, one aspect of the present invention is a complex of CoA, a beetle luciferase, and oxyluciferin its excited state on the enzyme.

The existence of the CoA-beetle luciferase-excited oxyluciferin complexes was not recognized heretofore. Such complexes occur in any solution in which CoA, luciferin, ATP, oxygen and a beetle luciferase in an enzymatically active form, are together, including in vitro (e.g., in a solution of the luciferase being used in an assay) and in the cells of light organs of beetles, in which bioluminescence is generated in the luciferase-luciferin reaction. In the present application it is intended to claim the CoA-enzyme-excited oxyluciferin complex of a beetle luciferase only outside the environment, in which the complex occurs in nature, i.e., outside cells, in which the luciferase occurs in nature, in the beetle.

It has been found that beetle luciferases catalyze formation of the thioester of CoA and luciferin, luciferyl-CoA. The existence of this compound also has not been recognized heretofore. Thus, this thioester is another aspect of the invention.

Similar to the complex of CoA-beetle luciferase-excited oxyluciferin, luciferyl-CoA occurs in any solution in which luciferin, ATP, CoA and a beetle luciferase, in an enzymatically active form, are together, including in vitro (e.g., in a solution of the luciferase being used in an assay) and in the cells of light organs of beetles, in which bioluminescence is generated in the luciferase-luciferin reaction. In the present application it is intended to claim the luciferyl-CoA only outside the environment, in which the compound occurs in nature, i.e., outside cells, in which a luciferase occurs naturally. Luciferyl-CoA is a compound that is important in mediating the beneficial effects of CoA on the kinetics of light production in the beetle luciferase-luciferin reaction. Formation of the thioester is involved in the reduction, in the presence of CoA, of product inhibition in the luciferase-luciferin reaction.

The fate of luciferyl-CoA after it is made remains unclear, but it is possible that the thioester remains complexed to the enzyme and that CoA is regenerated from the thioester in the course of catalysis of the beetle luciferase-luciferin reaction.

It is believed that thiol reagents, i.e., substances such as DTT or $\beta$-ME, or the like, with free thiol groups which function as reductants, interact in some way with beetle luciferases, or with a product of catalysis by the enzymes, while they catalyze production of luminescence. The effect of such reagents on the luciferases, through this interaction during catalysis, appears to saturate at a concentration about 10 times to about 100 times higher than the concentration at which the effect of CoA saturates. By this interaction during catalysis of thiol reagent with the enzyme or a product of catalysis by the enzyme, the reagent slows inactivation of the enzyme from the rate at which the inactivation would occur in the absence of thiol reagent.

CoA is both a substrate of the enzyme, with a specific binding site associated with such role, and a thiol reagent, with associated enzyme-activity-stabilizing properties. With CoA the situation might be even more complicated, as it is possible that, in connection with slowing the rate of product inhibition during the luciferase-luciferin reaction, CoA increases the rate of enzyme inactivation that occurs during the reaction. CoA, at a concentration in excess over that required to saturate the CoA substrate binding site during catalysis, would then also, like other thiol reagents, slow the rate of inactivation.

The effect of CoA on the kinetics of beetle luciferase-luciferin reactions saturates at relatively low CoA concentrations, between about 0.1 mM and about 1 mM, which is a range typical for saturation of binding to an enzyme by a substrate.

The effect of thiol reagents, other than CoA, on the kinetics of beetle luciferase-luciferin reactions is not suggested by the prior art. The effect saturates at between about 30 mM and about 80 mM, much higher concentrations than the 1 mM-5 mM suggested in the art to protect the proteins from inactivation during preparation and storage and much higher than the 0.1 mM-1 mM at which the effect of CoA on such kinetics saturates. The stabilizing effect of the thiol reagents is not simply due to protection against oxidation of the enzyme generally, as suggested by the prior art. Above 5 mM, the thiol reagents have no stabilizing effect on the enzyme in the absence of catalysis of the bioluminescence reaction, as the reagents would have if the stabilization were due simply to protection generally against oxidation of groups on the enzyme, but do stabilize the enzyme while such catalysis is proceeding.

Thus, the invention provides luciferase compositions, in which, in the luciferase-luciferin reaction, the kinetics of light production are improved as a consequence of reduced product inhibition or reduced inactivation of the luciferase. One such composition is an aqueous solution which comprises a beetle luciferase, CoA at between about 0.1 mM and 1.0 mM, and a thiol reagent other than CoA at between about 10 mM and about 100 mM. The composition may also comprise other substances such as ATP at between about 0.1 mM and 1.0 mM; luciferin at between about 0.1 mM and 1.0 mM; $Mg^{+2}$ ion at between about 2 mM and about 15 mM; phosphate ion, 2-aminoethanol or other peak-intensity-reducing compounds at concentrations effective to reduce peak intensity by up to about 30%; a buffer, such as tricine, HEPPS, HEPES, MOPS, Tris, glycylglycine, a phosphate salt, or the like, to maintain the pH and ionic strength of the solution in ranges at which the beetle luciferase is active in the luciferase-luciferin reaction; a proteinaceous luciferase-activity enhancer, such as a mammalian serum albumin or lactalbumin or an ovalbumin, preferably bovine serum albumin, at between about 10 $\mu$g/ml and 5 mg/ml; and EDTA or CDTA at between about 0.1 mM and about 1 mM. Any luciferin in such composition of the invention is preferably synthetic.

In still other aspects, the invention provides methods and test kits for detecting ATP in samples thought to contain the compound. These methods and kits of the invention rely on bioluminescence from a beetle luciferase-luciferin reaction and employ compositions whereby, in accordance with the invention, the kinetics of light production from such a reaction is improved.

In compositions of the invention, or used in methods of the invention, which are aqueous solutions and in which luciferin is present, the luciferin is typically present in a concentration of about 0.1 mM about 1 mM, preferably about 1 mM. Similarly, in such compositions in which ATP is present, the ATP concentration ranges from about 0.1 mM to about 5 mM, preferably about 0.5 mM. When CoA is present in such compositions, of or used in the invention, which are aqueous solutions, the concentration of CoA ranges from about 0.001 mM to about 1 mM, preferably about 1 mM. Similarly, the concentration of DTT present is from about 20 mM to about 200 mM, preferably about 30 to 40 mM, and that of BSA is from about 0.5 mg/ml to about 5 mg/ml, preferably about 1 mg/ml.

The luminescence of the luciferin-luciferase reaction may be measured using a commercially available luminometer, a scintillation counter, a photomultiplier photometer or a photoemulsion film.

To initiate a beetle luciferase-luciferin reaction in accordance with invention in a reaction solution, the reaction solution can be made by simple mixing of (usually two) solutions or by injection of one solution into another to accomplish very rapid mixing of the two. The use of thiol reagents in accordance with the present invention permits the need for a rapid-mixing (injection) format to be avoided in most cases.

The method of the present invention was tested by a variety of experiments designed to compare light production from conventional luciferase assays with assay methods in accordance with the present invention.

Figure 1:
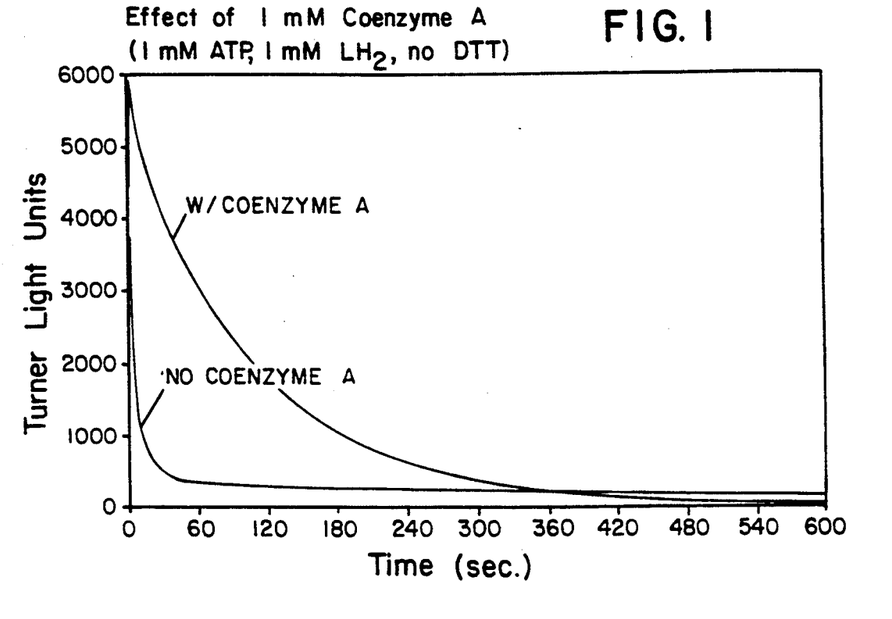
FIG. 1 is a graph comparing the luminescence due to beetle luciferase activity in the presence and absence of coenzyme A.

The effect of CoA on light production was compared to light production in its absence. The cofactor was added to the enzyme before mixing. In these tests, 100 $\mu$l of a solution containing 3 mM luciferin, 3 mM ATP, with or without 3 mM CoA in a buffer which consists of 25 mM Tricine, 7 mM $Mg^{2+}$, and 1 mM EDTA was injected into 200 $\mu$l of a solution containing 0.8 Nm luciferase in the same buffer as described above for the luciferin solution. FIG. 1 depicts the luminescence of luciferase with and without the presence of CoA. The total amount of light emitted by a reaction was estimated by integrating the intensity of the exponential decay extrapolated to infinite time. These data show that the addition of CoA to the assay mixture yields a greater initial light intensity with a lower initial decay rate, and more than a two-fold increase in total luminescence. Such data are unexpected, particularly in view of the fact that synthetic luciferin was employed.

Figure 2:
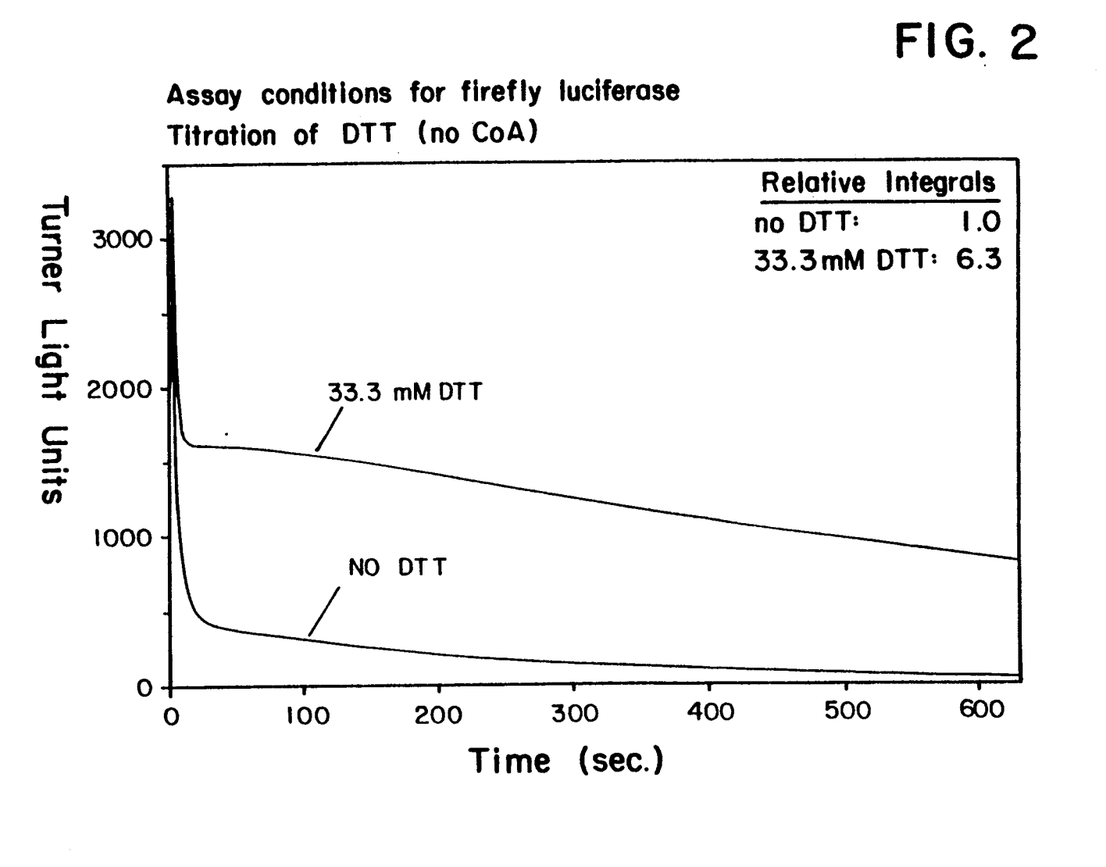
FIG. 2 is a graph comparing the luminescence due to beetle luciferase activity in the presence and absence of dithiothreitol.

The effects of other reagents possessing sulfhydryl groups were tested. FIG. 2 depicts the luminescence curve with 33.3 mM DTT present in the assay mixture. In this test, 100 μl of a solution containing 3 mM luciferin, 3 mM ATP and 100 mM DTT in the same buffer, as described in the immediately preceding paragraph for the experiments with CoA, was injected into 200 μl of 0.8 nM luciferase in the same buffer. The curve shows a much higher "steady-state" and total light production was increased 6.3 times over that without DTT present. Preincubation of DTT with the enzyme was also tested. Addition of 10 mM of DTT to the enzyme before assay resulted in no significant increase in light production. The results with other thiol reagents are similar to those found for DTT.

Figure 3A:
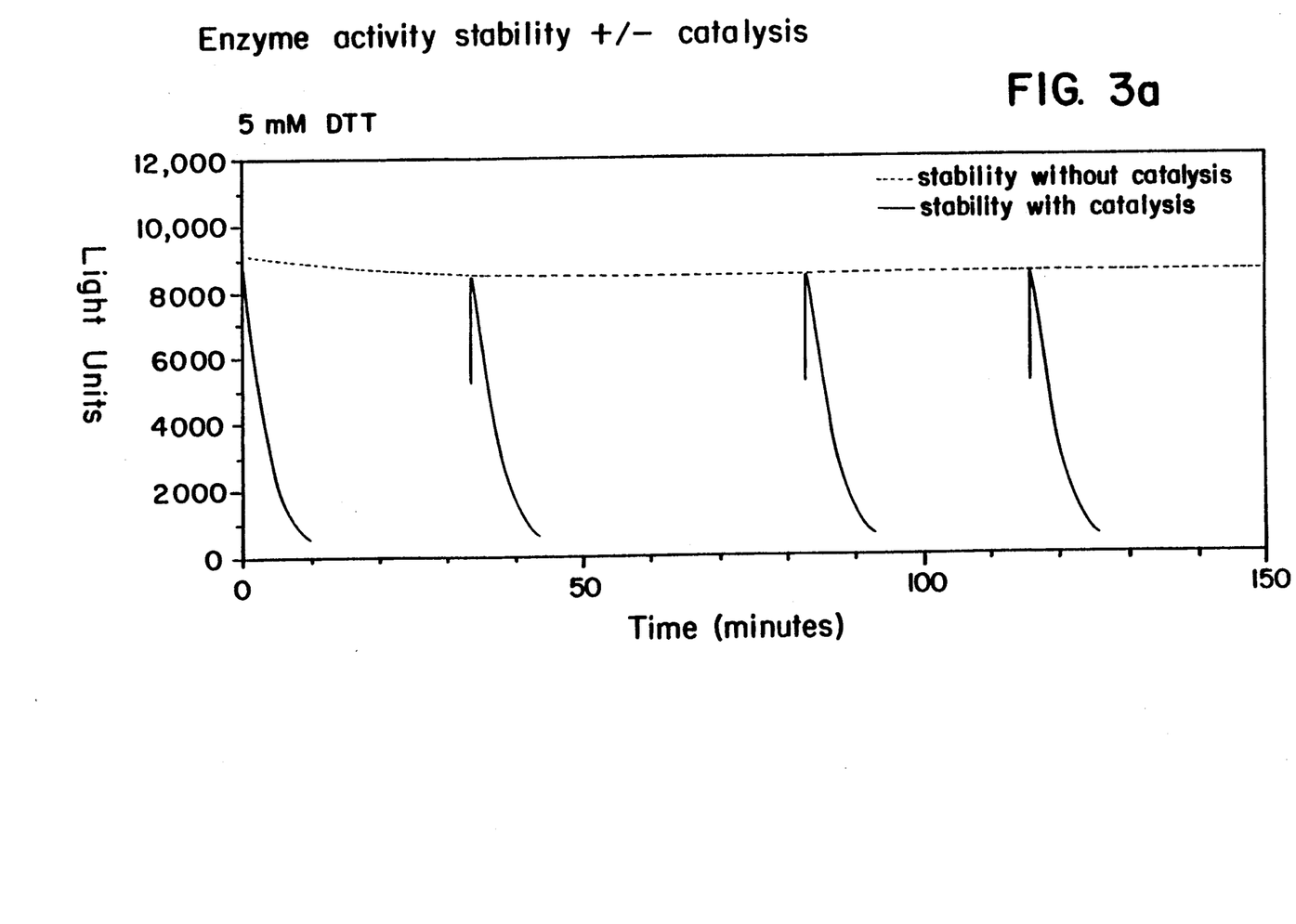
FIGS. 3a and 3b are graphs illustrating the effect of variation in concentration of dithiothreitol on beetle luciferase stability in the absence of catalysis and during catalysis of light production by the beetle luciferase-luciferin reaction.
Figure 3B:
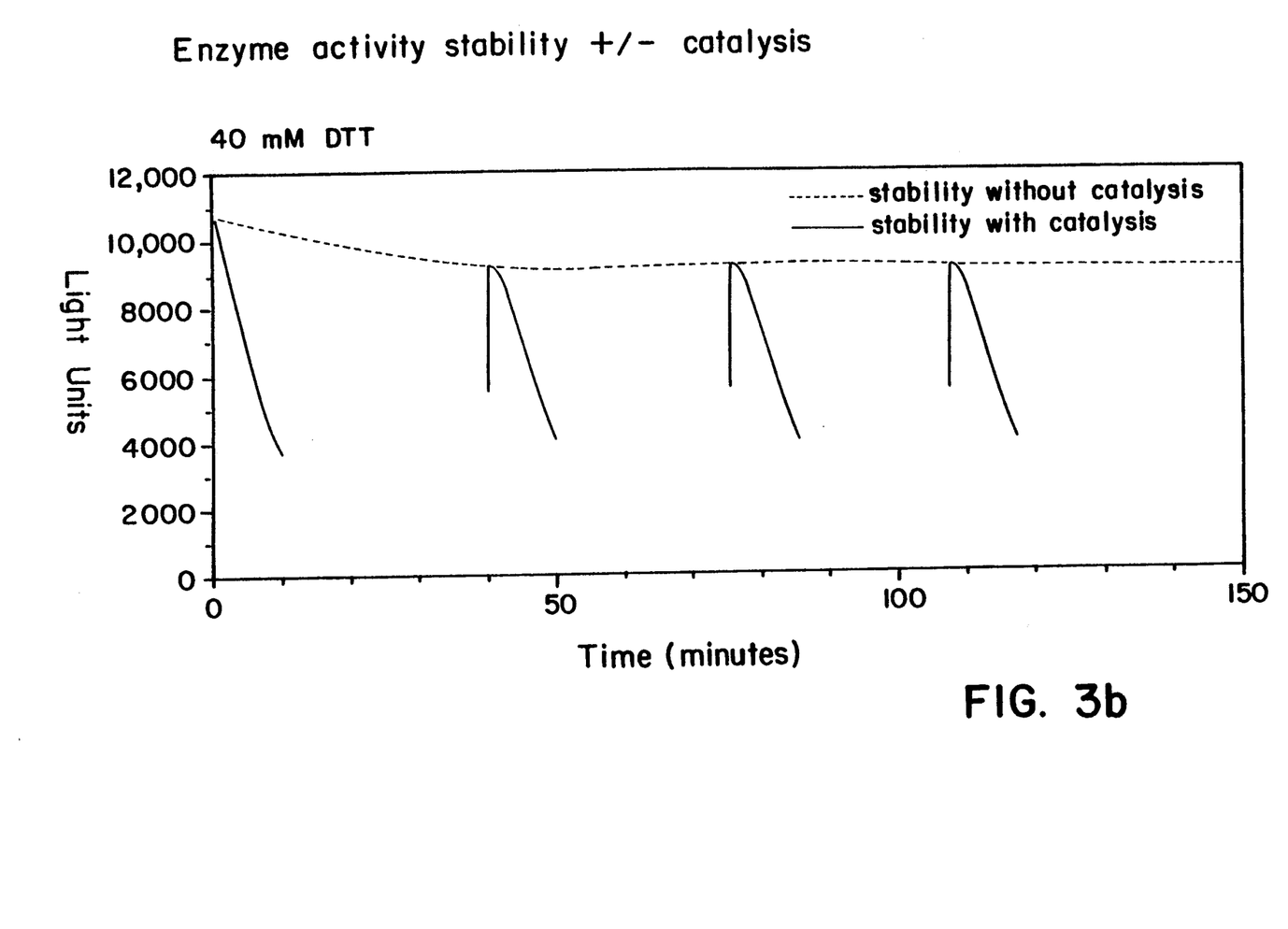

Tests were also performed to test the mode of action of DTT as compared to protective effects of thiols generally reported in the prior art. In these tests, two 1000 μl solutions were prepared containing 20 mM Tricine at pH 7.8, 8 mM $Mg^{2+}$, 0.13 mM EDTA, 0.53 mM ATP and 0.27 mM CoA; one of the solutions also contained 5 mM DTT while the other contained 40 mM DTT. An equal aliquot of luciferase was added to each. At various times, 200 μl of solution were removed and luciferin was added to a concentration of 0.47 mM to initiate enzyme activity. The condition of the luciferase solutions is the same as the reaction conditions except that luciferin is not present so catalysis cannot proceed. Light output was measured for 10 minutes. The results are depicted in FIGS. 3a and 3b. Two conclusions may be drawn from these results—first, the stability of enzyme activity is much reduced during catalysis and second, the increase of DTT concentration above 5 mM does not increase the stability of luciferase in the absence of catalysis, but does increase stability during catalysis. It is likely that DTT acts by different modes on the enzyme when it is not catalyzing the luciferase-luciferin reaction and when it is catalyzing the reaction.

Tests were also performed to test the effects of other additives. For example, BSA increased light intensity about 20%, but did not change the rate of decay. Increased initial light intensity was also found with the addition of a nonionic surfactant, Triton X-100, but was followed by an increased rate of decay. Other nonionic surfactants appeared to have little effect on enzyme activity.

Figure 4:
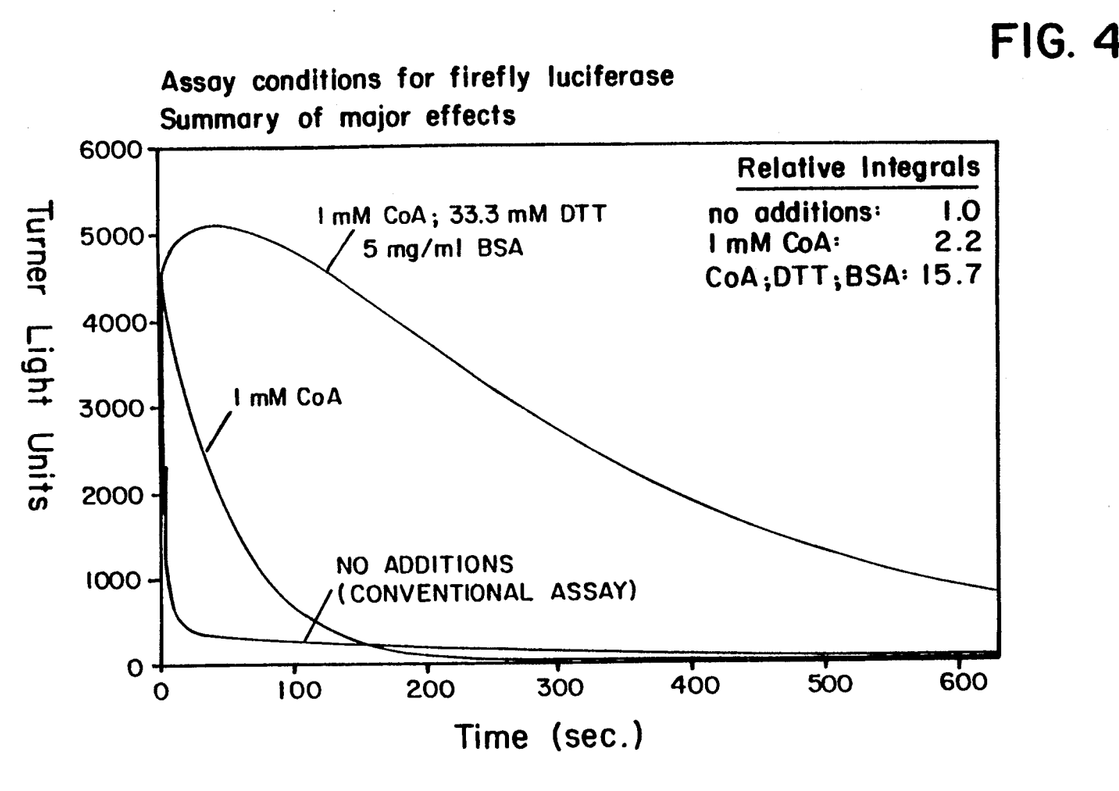
FIG. 4 is a graph comparing the luminescence due to beetle luciferase activity in the presence of coenzyme A, dithiothreitol and bovine serum albumin with the luminescence due to such activity in the absence of coenzyme A, dithiothreitol, and bovine serum albumin.

FIG. 4 depicts the luminescence curves in which a combination of CoA, DTT and BSA were present in the assay, CoA alone was present in the assay, and there were no additions to the conventional assay. The combined effect of CoA, DTT and BSA resulted in total light production greater than 15 times that with no additions.

A surprising result of the method of the present invention is that an increase in total luminescence of 15-to 17-fold over 10 minutes can be effected compared to luminescence in the absence of the thiol reagents and enzyme stabilizer. The combined effect of these agents enhances the utility of luciferases as reporters. Improved light production permits a highly sensitive, rapid method of detecting products or events in certain biospecific reactions.

The present invention is further explained by the following examples which should not be construed by way of limiting the scope of the present invention.

EXAMPLE 1

A kit for detecting the synthesis of luciferase in foreign hosts was prepared which consisted of a lysing reagent and an assay reagent. The lysing reagent consisted of 25 mM Tris-phosphate at pH 7.8, 10% glycerol (which could have been replaced with ethylene glycol), 1% Triton X-100 (trademark of Rohm & Hass Corp. for a non-ionic detergent which is an octoxynol mixture with the average number of ethylenyloxy ($-CH_2C-H_2O-$) units per molecule between 9 and 10), 1 mg/ml of bovine serum albumin (BSA), 2 mM CDTA (cyclohexylenediaminetetraacetate) and 2 mM DTT. The assay reagent consisted of 20 mM tricine (N-tris(hydroxymethyl) methyl glycine) buffer at pH 7.8, 33.3 mM DTT, 8 mM $Mg^{30\ 2}$, 0.13 mM EDTA, 0.53 mM ATP, 0.47 mM luciferin and 0.27 mM CoA.

A cellular extract was derived from NIH 3T3 cells containing plasmid pRSVL, a plasmid containing a CDNA encoding P. pyralis firefly luciferase under transcriptional control of the 5'-LTR of proviral DNA corresponding to the Rous sarcoma virus genome. The cells were grown to about one third confluency in a 100 mm petri dish. The cells were then transformed with 10 μg of plasmid DNA using the standard calcium phosphate method known in the art, and grown for an additional 48 hours.

The cultured cells were lysed by addition 1 ml of lysing reagent at room temperature for 2 to 5 min. After lysis, the cellular debris was removed by brief centrifugation, about 10 sec, and the supernatant (i.e., the solution of cellular extract) was tested for luciferase activity.

The enzyme activity was tested by mixing the cellular extract with the assay reagent in a ratio of between about 1:5 and 1:25, cellular extract:assay reagent. Injection was not used in carrying out the mixing.

Luminescence of the cell extract-luciferin reaction in accordance with the assay of the present invention was compared with a conventional assay for luciferase activity. The comparison was performed using an injection-type format for mixing, as required in the conventional, prior art assay, although the assay of the present invention does not require an injection procedure. In these comparisons, 100 μl of a solution containing 0.8 mM CoA, 1.4 mM luciferin, 1.5 mM ATP and 90 mM DTT in a buffer of 20 mM tricine, 8 mM $Mg^{+2}$, 0.13 mM EDTA, pH 7.8, was injected into 220 μl of a solution made by mixing 20 μl of cellular extract with 200 μl of buffer (20 mM tricine, 8 mM $Mg^{+2}$, 0.13 mM EDTA, pH 7.8) and the luminescence was measured using a standard luminometer (e.g., a Turner Model 20 luminometer). The comparison conventional assay, which is an adaptation of the assay published in the first reports of luciferase used as a reporter of genetic events, such as transcription, Mol. Cell. Biol. 7, 725-737 (1987), Science 234, 856-859 (1986), consisted of injecting 100 μl of a solution containing 0.67 mM luciferin in a buffer of 25 mM glyclyglycine, 12 mM $Mg^{+2}$, pH 7.8, into 220 μl of a solution made by mixing 20 μl of cellular extract with 200 μl buffer (25 mM glyclyglycine, 12 mM $Mg^{+2}$, pH 7.8) having 5.83 mM ATP.

Figure 5:
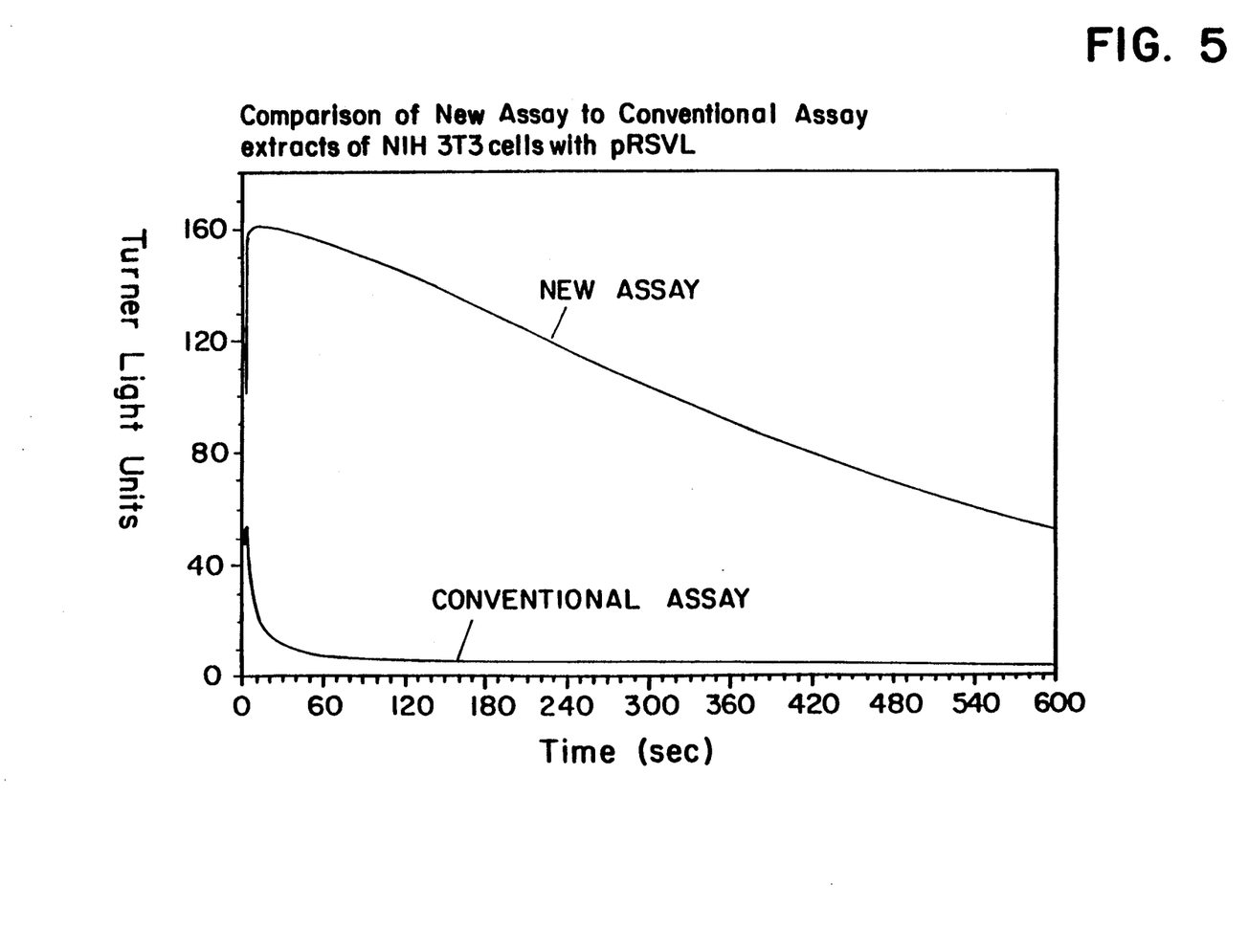
FIG. 5 is a graph comparing the luminescence in an assay in accordance with the present invention with that in a conventional, prior art assay due to beetle luciferase activity in extracts from mammalian cells in culture, in which the luciferase was produced by expression of a CDNA encoding the enzyme.

FIG. 5 depicts the results of these tests. In the graphs in FIG. 5, the intensity of luminescence is plotted as a function of time from the time of injection. The results demonstrate that the assay in accordance with the present invention yielded a 10-fold increase in light output (i.e., luminescence produced) over the conventional assay, when output was determined by integration of the intensity vs. time curve from 0 to 60 seconds, and a 17-fold increase in luminescence produced in comparison with the conventional assay, when the output was determined in an integration of the intensity vs. time curve from 0 to 5 minutes. The absence of the sharp peak in intensity in the assay in accordance with the invention, in comparison with the conventional assay, is also apparent in FIG. 5.

EXAMPLE 2

A 1 mg/ml stock luciferase solution was prepared from crystalline pure, *P. pyralis* luciferase in 10% ammonium sulfate and 10% glycerol. Luciferase solutions used for reaction purposes were prepared from the stock solution by 100-fold consecutive dilutions into the lysing reagent described in Example 1. From each dilution, 20 μl was added (without injection) to 200 μl of the assay reagent described in Example 1 and placed in a standard luminometer for measurement of the light emission.

Figure 6:
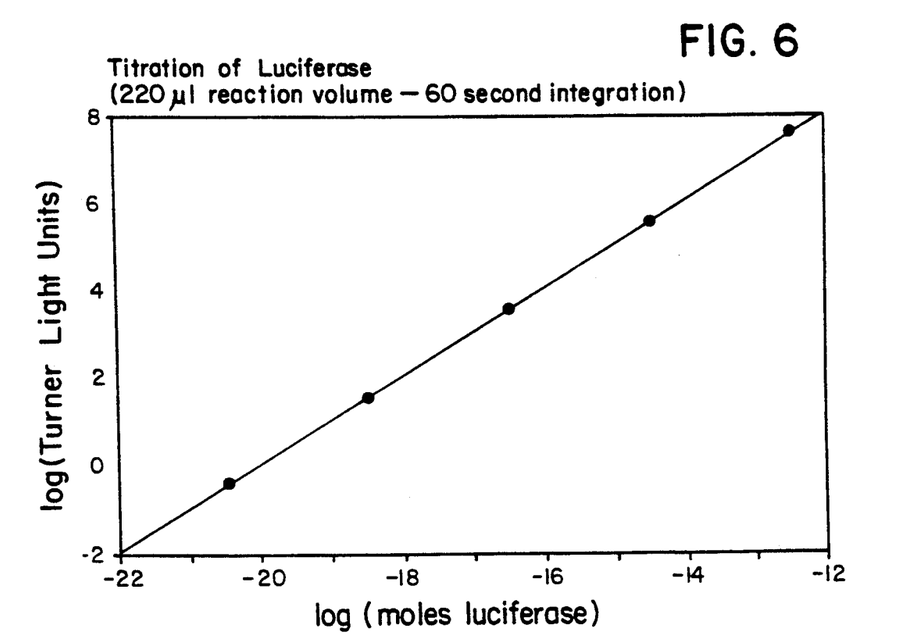
FIG. 6 is a graph illustrating both (1) the linear relationship between the logarithm of the concentration of beetle luciferase and the logarithm of light produced in the beetle luciferase-luciferin reaction in assays carried out in accordance with the present invention and (2) the sensitivity of such assays in detecting beetle luciferase.

FIG. 6 is a plot of the log of the luminescence produced (as measured by integration of luminescence intensity for 60 seconds) as a function of the log of the luciferase concentration for the various samples. The curve in FIG. 6 shows excellent linearity over 8 orders of magnitude of luciferase concentration. The concentration of luciferase for the data point on the graph of FIG. 6 representing the lowest such concentration is 50-times lower than the lowest concentration of luciferase detectable in the most sensitive assays for luciferase reported heretofore. Such high sensitivity is achieved with the present invention because of the increase in luminescence produced in comparison with the prior art systems and the "flat" kinetics, which allows the effects of random noise in the light-measuring device to be averaged out.

In the experiment described in this Example, the kinetics of light production at all concentrations of luciferase were nearly flat. Also, the coefficient of variation for measurements at each concentration (5 replicas) were better than 1.5%, except at the lowest concentration, where signal from noise in the luminometer became significant. This level of precision is equivalent to or better than that generally reported for the prior art, injection-type assays.

Based on the linearity displayed by the curve in FIG. 6, the precision with which the data points for the curve could be measured, and the experiment reported in Example 4 on a relatively concentrated luciferase solution (approx. 1 μM), the practical range of luciferase concentrations for the assays of the present invention extends from the lowest that light-detecting instrumentation, with the lowest possible background, can detect (presently about $10^{-18}$ to $10^{-17}$ M, or about 200 molecules of the enzyme in a 200 μl volume of solution) up to about 10 μM. The concentration of a luciferase in any sample of practical interest will be well inside this range.

EXAMPLE 3

In this example, illustrations are provided of the advantageous effect, on total luminescence from a luciferase-luciferin reaction in the presence of CoA, of reducing by a small amount the peak intensity of luminescence from the reaction.

Figure 7:
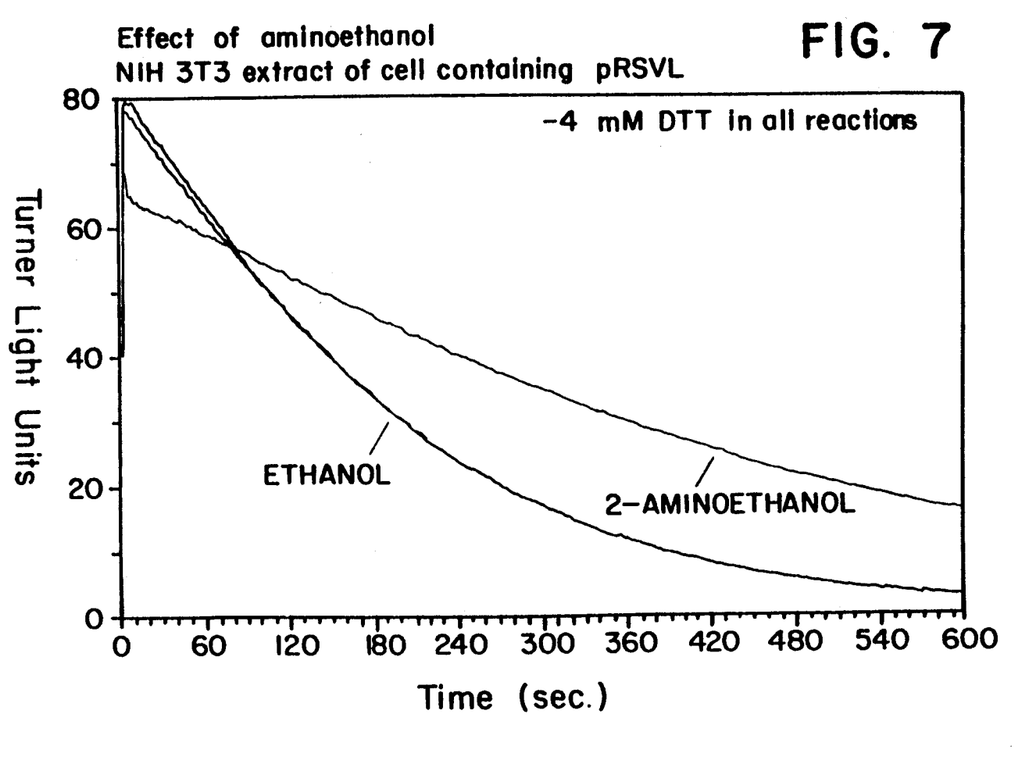
FIG. 7 is a graph illustrating the effect of 36 mM 2-aminoethanol and the lack of effect of 36 mM ethanol on light production from a beetle luciferase-luciferin reaction carried out in the presence of CoA.

FIG. 7 illustrates that including the luciferase inhibitor 2-aminoethanol at 36 mM in a luciferase-luciferin reaction mixture which includes CoA reduces the peak intensity of the luminescence by about 12% and increases yield of luminescence, as measured by integration of luminescence intensity for more than about 3 minutes from initiation of the reaction.

Figure 8:
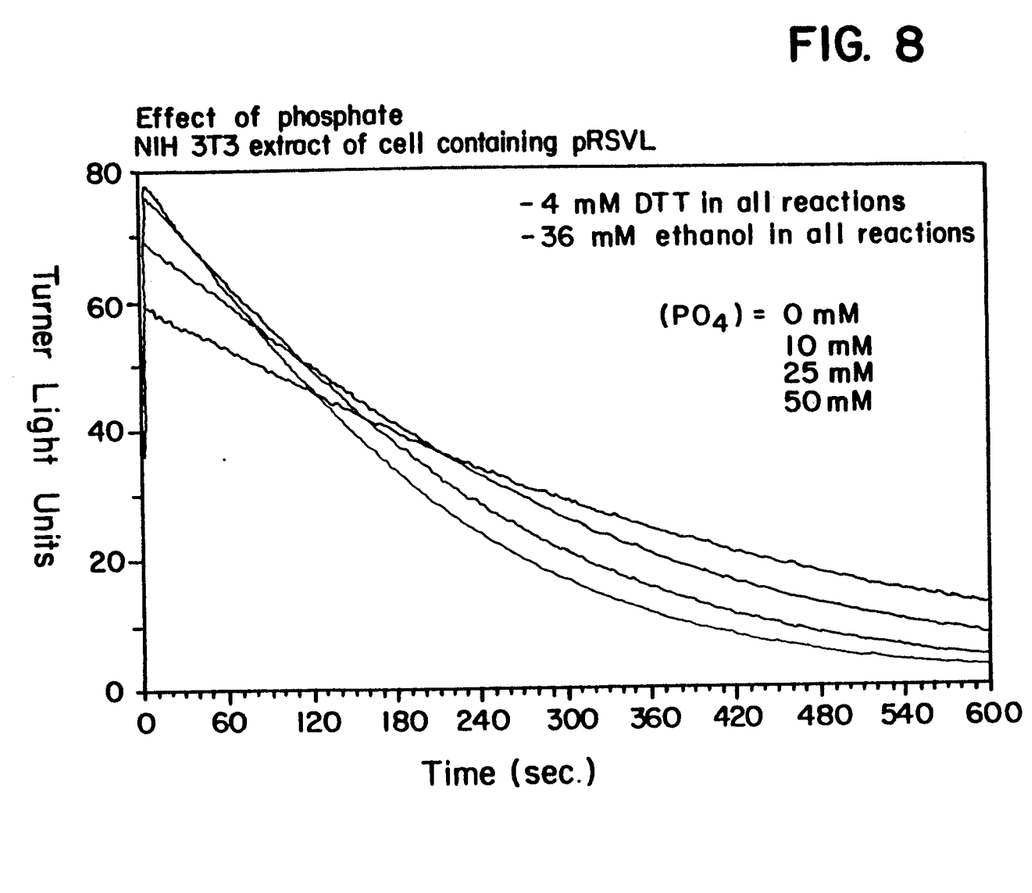
FIG. 8 is a graph illustrating the effects of various concentrations of phosphate on light production from a beetle luciferase-luciferin reaction carried out in the presence of CoA. In the graph, the peak intensity decreases as the phosphate concentration increases.

Similarly, FIG. 8 shows that including phosphate, also a luciferase inhibitor, in a luciferase-luciferin reaction mixture which includes CoA reduces peak intensity of luminescence (by a percentage that depends on the phosphate concentration) but increases total luminescence, when measured by integration of luminescence intensity over a time period that differs with phosphate ion concentration. Higher phosphate concentrations depress peak intensities to a greater extent and require integration of intensity over longer periods of time to make evident the increase in total luminescence.

The data for FIGS. 7 and 8 were obtained using the methods described in Example 1, in comparing assays according to the invention with conventional, prior art assays for luciferase in cellular extracts, except that 100 μl of a solution of 0.8 mM CoA, 1.4 mM luciferin, 1.5 mM ATP, 8 mM $Mg^{+2}$, 0.13 mM EDTA, 5.5 mM DTT, 20 mM tricine, pH 7.8, and, in addition, (1) no other compound or (2) 110 mM 2-aminoethanol or (3) 110 mM ethanol or (4) 110 mM ethanol together with 30 mM, 75 mM or 50 mM sodium phosphate was injected into 220 μl of a solution made by mixing 20 μl of cellular extract with 200 μl of buffer (20 mM tricine, 8 mM $Mg^{+2}$, 0.13 mM EDTA, pH 7.8) and the luminescence was measured using a standard luminometer. As indicated in FIGS. 7 and 8, 36 mM ethanol has no significant effect on production of luminescence in the luciferase-luciferin reaction in the presence of CoA.

EXAMPLE 4

In this Example, support is provided for the facts that, in the beetle luciferas-luciferin reaction in the presence of CoA, (1) luciferyl-CoA, the thioester between the carboxyl of luciferin and the sulfur of the thiol group of CoA, is formed and (2) a complex of the luciferase with CoA and oxidized luciferin in the exited state is also formed.

Comparison of amino acid sequences of beetle luciferases with those of other proteins reveals significant homology, and therefore common ancestry, with the plant enzyme, 4-coumarate:CoA ligase, and the enzyme long-chain acyl-CoA synthetase. Hydropathy plots (Kyte and Doolittle, J. Mol. Biol. 157, 105–132 (1982), averaging 15 residue values for each point) comparing the luciferases with the other two enzymes show similarities, with the similarity with the 4-coumarate:CoA ligase being especially striking. Both the 4-coumarate:CoA ligase and the long chain acyl-CoA-synthetase catalyze formation of thioesters between CoA and carboxyl groups of their respective substrates. With both enzymes, ATP reacts with a substrate to form an acyl-AMP intermediate in formation of the thioester. As indicated above, luciferase similarly forms luciferyl adenylate from ATP and luciferin.

In the studies in the 1950's, on the effect of CoA on the kinetics of light production in the beetle luciferase-luciferin reaction, it was shown that the non-oxidizable luciferin analog, dehydroluciferin, could form a thioester bond through its carboxyl group with CoA.

It has now been found that the activity of CoA, in affecting the kinetics of light production in the beetle luciferase-luciferin reaction, is mediated specifically through its thiol group. DethioCoA is identical to CoA without the sulfur atom. When dethioCoA, rather than CoA, was added to a luciferase-luciferin reaction mixture, there was no effect on the kinetics of light production from the reaction. Further, the increase in light production in such a reaction caused by CoA is specifically inhibited by dethioCoA. On reciprocal plots, of the reciprocal of the increase in light production as a function of the reciprocal of CoA concentration, with and without dethioCoA at a constant concentration, the dethioCoA displayed activity as a competitive inhibitor of CoA. Thus, dethioCoA and CoA bind to the same site on luciferase but dethioCoA, lacking the thiol group, has no CoA-like activity.

In the experiments to obtain the reciprocal plots, buffer for the luminescence assays was 30 mM tricine, 8 mM magnesium carbonate, 10 mM DTT, 0.2 mM EDTA, pH 7.8. Crystalline *P. pyralis* luciferase, at 10 mg/ml in 10% ammonium sulfate and 50% glycerol, was diluted 10,000-fold into the buffer supplemented with 10% (v/v) glycerol and 1 mg/ml bovine serum albumin. Then, for an assay, 10 µl of the enzyme dilution (enzyme at 1 µg/ml) was mixed with 200 µl of the buffer; luminescence was initiated by injection, into the resulting 210 µl, of 100 µl of buffer supplemented with 3 mM luciferin, 1.5 mM ATP, and various concentrations of CoA and dethioCoA (with 3 mM dethioCoA: 0.012 mM, 0.06 mM, and 0.3 mM CoA; with no dethioCoA: 0.012 mM, 0.06 mM, 0.3 mM CoA, and 1.0 mM CoA). Luminescence was measured on a Turner Model 20 luminometer.

The presence of CoA in a solution in which light is being produced by a beetle luciferase-luciferin reaction has been discovered to shift to shorter wavelength the color of the light being produced. The color of this light is determined by the difference in energy between enzyme-bound, oxidized luciferin in the excited state and enzyme-bound, oxidized luciferin in the ground state. The shift to shorter wavelength means that, on the average among the complexes of oxidized luciferin and luciferase, this difference in energy is increased by CoA. For such increase in energy to occur, there must exist a complex of the enzyme with CoA and oxidized luciferin in the excited state, which causes an increase in the fraction, relative to that in the absence of CoA, of complexes of the enzyme with excited oxyluciferin in which the difference in energy between the excited and ground state oxyluciferin is higher. That the effect of CoA in such a complex would be to alter the structure of the luciferase-oxyluciferin complex would be consistent with the observation, noted above, that luciferases of differing amino acid sequences and therefore at least slightly different three-dimensional structures, e.g., from different species of beetles, catalyze production of bioluminescence of different colors.

The discovery that CoA decreases the wavelength of light produced in the beetle luciferase-luciferin reaction was made in the following experiment with P. pyralis luciferase. In these comparisons, a first solution was prepared by mixing 250 µl of a solution containing 0.8 mM CoA, 1.4 mM luciferin, 1.5 mM ATP and 90 mM DTT in a buffer of 20 mM tricine, 8 mM Mg$^{+2}$, 0.13 mM EDTA, pH 7.8, with a solution that had been made by mixing 0.5 µl of a solution of *P. pyralis* luciferase (10 mg/ml in 10% ammonium sulfate, 50% glycerol) with 500 µl of buffer (20 mM tricine, 8 mM Mg$^{+2}$, 0.13 mM EDTA, pH 7.8). A second solution was prepared in the same way, except without any CoA or DTT. The first and second solutions were observed by eye while light from the luciferase-luciferin reaction was being produced. The first solution was slightly, but distinctly, greener in color than the second solution.

While the present invention has now been described and exemplified with some specificity, those skilled in the art will appreciate the various modifications, including variations, additions and omissions, that may be made in what has been disclosed herein without departing from the spirit of the invention. Accordingly, it is intended that these modifications also be encompassed by the present invention and that the scope of the present invention be limited solely by the broadest interpretation that lawfully can be accorded the appended claims.

I claim:

1. In a method for detecting the presence of a beetle luciferase in a sample suspected of containing the luciferase, comprising:
   (a) making with an aliquot of said sample a solution comprising, at concentrations effective for activity of the luciferase in the luciferin-luciferase reaction, luciferin, ATP and Mg$^{2+}$; and
   (b) measuring luminescene from the solution resulting from step (a),
   the improvement which comprises having in the solution resulting from step (a) a thiol reagent other than CoA at a concentration between 20 mM and 200 mM.

2. The improvement of claim 1 wherein, in the solution resulting from step (a), the thiol reagent other than CoA is selected from the group consisting of dithiothreitol, dithioerythritol, β-mercaptoethanol, 2-mercaptopropanol, 3-mercaptopropanol, 2,3-dithiopropanol, and glutathione.

3. The improvement of claim 2 wherein the solution resulting from step (a) comprises CoA.

4. The improvement of claim 3 wherein the solution resulting from step (a) additionally comprises a proteinaceous luciferase-activity enhancer.

5. The improvement of claim 3 wherein the thiol reagent other than CoA is dithiothreitol.

6. The improvement of claim 4 wherein the thiol reagent other than CoA is dithiothreitol and the luciferase-activity enhancer is bovine serum albumin.

7. The improvement of claim 5 wherein, in the solution resulting from step (a), the concentration of CoA is between 0.01 mM and 1.0 mM.

8. The improvement of claim 6 wherein, in the solution resulting from step (a), the concentration of CoA is between 0.1 mM and 1.0 mM and the concentration of bovine serum albumin is between 10 µg/ml and 5 mg/ml.

9. The improvement of claim 7 wherein, in the solution resulting from step (a), the concentration of ATP is between 0.1 mM and 1 mM, the concentration of luciferin is between 0.1 mM and 1 mM, and the concentration of Mg$^{+2}$ is between 2 mM and 15 mM.

10. The improvement of claim 8 wherein, in the solution resulting from step (a), the concentration of ATP is between 0.1 mM and 1 mM, the concentration of luciferin is between 0.1 mM and 1 mM, and the concentration of $Mg^{+2}$ is between 2 mM and 15 mM.

11. The improvement according to any one of claims 2-10 wherein the beetle luciferase is the luciferase of *Photinus pyralis*.

12. The improvement according to any one of claims 7-10 wherein the concentration of dithiothreitol in the solution resulting from step (a) is between 30 mM and 80 mM.

13. The improvement according to claim 12 wherein the beetle luciferase is the luciferase of *Photinus pyralis*.

* * * * *